(12) United States Patent
Niccol (10) Patent No.: US 10,569,040 B2
(45) Date of Patent: Feb. 25, 2020

(54) INTERFACE SIZING TOOL AND METHOD

(71) Applicant: Fisher & Paykel Healthcare Limited, Auckland (NZ)

(72) Inventor: Andrew Grant Niccol, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 16/111,029

(22) Filed: Aug. 23, 2018

(65) Prior Publication Data

US 2019/0054267 A1 Feb. 21, 2019

Related U.S. Application Data

(63) Continuation of application No. 15/101,841, filed as application No. PCT/NZ2014/050018 on Dec. 5, 2014, now Pat. No. 10,058,670.

(60) Provisional application No. 61/912,384, filed on Dec. 5, 2013.

(51) Int. Cl.
  *A61M 16/06* (2006.01)
  *A61B 5/107* (2006.01)
  *A61B 5/00* (2006.01)

(52) U.S. Cl.
  CPC ............. *A61M 16/06* (2013.01); *A61B 5/107* (2013.01); *A61B 5/1072* (2013.01); *A61B 5/1079* (2013.01); *A61B 5/4836* (2013.01); *A61B 5/00* (2013.01); *A61B 2560/0418* (2013.01); *A61M 16/0605* (2014.02); *A61M 2016/0661* (2013.01); *A61M 2210/0606* (2013.01)

(58) Field of Classification Search
  CPC .......... A61M 16/06; A61M 2016/0661; A61M 16/0605; A61M 2210/0606; A61B 5/00; A61B 5/107; A61B 5/1072; A61B 5/1079; A61B 5/4836; A61B 2560/0418
  USPC .... 33/1 PT, 1 N, 275 R, 281, 282, 285, 286, 33/512, DIG. 21
  See application file for complete search history.

(56) References Cited

U.S. PATENT DOCUMENTS

| | | |
|---|---|---|
| 2,752,689 A | 7/1956 | Adams et al. |
| 3,692,414 A | 9/1972 | Hosterman et al. |
| 4,457,625 A | 7/1984 | Greenleaf et al. |
| 4,530,367 A | 7/1985 | Desjardins et al. |
| 4,575,805 A | 3/1986 | Moermann et al. |
| 4,677,428 A * | 6/1987 | Bartholow ............ G06F 3/0386 250/227.13 |
| 4,996,994 A | 3/1991 | Steinhauer et al. |
| 5,143,086 A | 9/1992 | Duret et al. |

(Continued)

OTHER PUBLICATIONS

PCT International Search Report, dated Feb. 27, 2015, in 3 pages.

*Primary Examiner* — Nimeshkumar D Patel
*Assistant Examiner* — Tania C Courson
(74) *Attorney, Agent, or Firm* — Knobbe, Martens, Olson & Bear, LLP (57) ABSTRACT

A method and apparatus can be used in the selection of correctly sized respiratory interfaces. The method includes the use of light beams to project sizing markers onto a patient's face, which enables the size of the patient's facial features to be measured relative to a set of interface sizes. A sizing apparatus can include a light source and beam splitters that will refract and project the light source into a series of beams that can be aligned on a patient's face in order to measure the features of the patient.

17 Claims, 5 Drawing Sheets

(56) References Cited

U.S. PATENT DOCUMENTS

| | | | | |
|---|---|---|---|---|
| 5,278,756 | A * | 1/1994 | Lemchen | A61C 19/04 |
| | | | | 128/920 |
| 5,598,269 | A * | 1/1997 | Kitaevich | A61B 6/08 |
| | | | | 356/399 |
| 5,617,304 | A | 4/1997 | Huang | |
| 5,691,799 | A | 11/1997 | Ramachandran | |
| 5,836,081 | A * | 11/1998 | Orosz, Jr. | A61B 5/0215 |
| | | | | 33/290 |
| 5,864,956 | A | 2/1999 | Dong | |
| 5,927,973 | A | 7/1999 | Hanebaum et al. | |
| 5,960,099 | A | 9/1999 | Hayes, Jr. et al. | |
| 6,006,126 | A * | 12/1999 | Cosman | A61B 34/20 |
| | | | | 600/414 |
| 6,509,973 | B2 * | 1/2003 | Kiyoi | G01B 11/24 |
| | | | | 356/601 |
| 6,728,589 | B1 | 4/2004 | Delache et al. | |
| 7,743,920 | B1 | 6/2010 | Lordo | |
| 7,903,245 | B2 | 3/2011 | Miousset et al. | |
| 8,162,852 | B2 * | 4/2012 | Norris | A61B 8/0841 |
| | | | | 600/567 |
| 9,307,930 | B2 | 4/2016 | Todd | |
| 9,347,758 | B2 | 5/2016 | Berent et al. | |
| 10,058,670 | B2 * | 8/2018 | Niccol | A61B 5/1072 |
| 10,130,433 | B2 * | 11/2018 | Popovic | A61B 90/13 |
| 2001/0037581 | A1 | 11/2001 | Akhavan-Sigari et al. | |
| 2003/0112220 | A1 * | 6/2003 | Yang | G06F 3/03545 |
| | | | | 345/156 |
| 2004/0189621 | A1 * | 9/2004 | Cho | G06F 3/03545 |
| | | | | 345/179 |
| 2011/0298912 | A1 | 12/2011 | Jelinek et al. | |
| 2013/0192071 | A1 | 8/2013 | Esposito et al. | |
| 2015/0273170 | A1 | 10/2015 | Bachelder et al. | |
| 2016/0067436 | A1 | 3/2016 | Grashow | |
| 2017/0280970 | A1 * | 10/2017 | Sartor | A61B 1/0676 |

* cited by examiner

FIG. 4 though all details in this disclosure, including what is shown in the figures, are intended for ease of understanding and explanation only.

INTERFACE SIZING TOOL AND METHOD

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57.

BACKGROUND

Field

The present disclosure generally relates to the selection of appropriately sized respiratory interfaces. More particularly, the present disclosure relates to a method and apparatus for selecting an appropriately sized respiratory interface for use in providing respiratory therapies, such as but not limited to positive airway pressure (PAP) therapies (e.g., constant positive airway pressure (CPAP) therapy) and non-invasive ventilation (NIV).

Description of Related Art

There exists tools and methods that are currently employed to select appropriately sized interfaces for patients. For example, a commonly known method and apparatus for selecting appropriately sized patient interfaces includes the use of cardboard or plastic sizing guides to measure a patient's face. Sizing guides usually consist of a piece of cardboard or plastic with markings and/or cut-outs that indicate interface sizes. The sizing guide is then held against a patient's face in order to measure their facial features in relation to the available interface sizes and select the most appropriate interface size.

SUMMARY

It is common for sizing guides not to be used when selecting an interface for a patient because of a number of problems related to traditional sizing guides. These problems can include hygiene or perceived hygiene, accessibility and ease of use. The sizing guides are often included as an insert or as a part of the interface packaging. Packaging can be handled by many people before the product reaches the patient, which may result in the sizing guide to be held against a patient's face being unhygienic or creating a concern in the patient that the sizing guide is unhygienic. It is also possible that a single sizing guide will be used to measure multiple patients. This situation may also create a concern in the patient that the sizing guide has not been properly cleaned between uses and, thus, is unhygienic. It is common for packaging to be thrown away in order to minimize storage space when a dealer or hospital has a large stock of interfaces. This means that traditional sizing guides are often thrown away with the packaging, which makes them inaccessible.

A traditional sizing guide may not be very easy to use because it can be cumbersome or overly flexible. If the guide is too large, it may be a nuisance to store and awkward to hold against a patient's face. If the sizing guide is too flexible, it may be difficult to hold against the patients face and to achieve an accurate measurement.

Ineffective sizing tools often result in a trial and error approach to selecting interfaces. Typically the treatment provider will start off by providing a patient with a medium size interface and change to a different size if necessary or desired. This results in a slow sizing process and, if the appropriate size is not identified and selected, can result in ineffective or less-than-optimal treatment and/or discomfort for the patient. In addition, this process can result in waste, such as interfaces requiring sterilization or disposal after being used for a short time on a patient for whom it is unsuitable.

The systems, methods and devices described herein have innovative aspects, no single one of which is indispensable or solely responsible for their desirable attributes. Without limiting the scope of the claims, some of the advantageous features will now be summarized.

Certain features, aspects and advantages of the present disclosure include a method and apparatus for measuring a patient's face and for selecting an appropriately sized respiratory interface. In some configurations, the method includes using a focused light source to project markers onto a patient's face that correspond with or otherwise indicate the sizes of a respiratory interface. The projected markers can then be used to measure the patient's face to select the appropriate interface size.

In some configurations, the apparatus includes a pen-like tool that contains at least one light source and provides a means for projecting beams of light at predetermined spacings onto a patient's face. In some configurations, one or more beam splitters are used to project a beam of light from the light source onto the patient's face.

By providing a tool in a pen-like form and by using light as a measurement tool, certain of the problems experienced by traditional sizing guides are addressed. The pen-like structure makes it convenient for the person fitting a patient with a mask to carry the tool with them in his or her pocket. Thus, the tool is more likely to be accessible. Having a specific sizing tool that is reusable reduces or eliminates the storage space required and makes it quicker and easier for medical practitioners, dealers or other service providers to size a patient. In at least some configurations, the method is non-contact in that the patient will not need to be touched by the sizing tool, the user of the sizing tool, or both in order to be measured. As a result, a single measurement tool can be used for multiple people without hygiene issues. Benefits of selecting the correct interface size for a patient the first time include reduced waste and improved comfort, convenience and treatment for the patient.

In some configurations, a method of measuring a patient's face in order to select an appropriately sized respiratory interface involves a light source used to project sizing markers onto a patient's face.

In some configurations, a hand-held apparatus for mask sizing comprises a light source and means of refracting and projecting markers onto a patient's face, wherein the hand-held apparatus is spaced away from the patient's face in use. In some configurations the hand held apparatus comprises one or more light manipulation arrangements that are configured to manipulate light from the light source and project one or more markers onto a patient's face when the hand-held apparatus is spaced away from the patient's face. The one or more markers corresponds to a size of the interface.

In some configurations, an interface sizing tool comprises a body and a light source supported relative to the body. The light source is configured to project a beam of light. One or more light manipulation arrangements manipulate the beam of light to project one or more markers onto the face of a patient. A location of the one or more markers corresponds to an interface size. The light manipulation arrangements can affect one or more properties of the light beam.

In some configurations, each of the one or more markers is a beam of light.

In some configurations, multiple light manipulation arrangements are provided.

In some configurations, the beam of light from the light source passes through the multiple light manipulation arrangements, each light manipulation arrangement configured to partially manipulate the beam of light from the light source to generate the one or more markers.

In some configurations, the light manipulation arrangement is a beam splitter.

In some configurations, each marker is generated by splitting the beam of light from the light source into the one or more markers.

In some configurations, the multiple beam splitters are spaced apart from one another on the body.

In some configurations, the beam splitters are shaped and spaced such that the markers are spaced a predetermined distance from one another.

In some configurations, the spacing of two or more of the multiple markers corresponds to the size of the interface.

In some configurations, at least one lens is positioned in front of one or more of the beam splitters and configured to focus the marker light beam.

In some configurations, a reference marker is generated by a reference beam splitter.

In some configurations, each of the beam splitters refract only a portion of the incident beam of light from the light source such that all of the markers are visible on the face of the patient.

In some configurations, at least one of the beam splitters is movable along a length of the body.

In some configurations, the at least one movable beam splitter is movable to two or more positions corresponding to two or more interface sizes.

In some configurations, the body comprises a track and at least one platform movable within the track, wherein the each of the at least one movable beam splitters is carried by one of the movable platforms.

In some configurations, a mechanism for moving the at least one movable beam comprises a push button, a twist knob or a sliding switch.

In some configurations, the body comprises a clip that permits the tool to be attached to an object by the clip.

In some configurations, the tool comprises a laser pointer or writing tip.

In some configurations, a method of sizing a patient for an interface comprises projecting one or more markers generated by a light source onto the face of a patient. The size of an interface to be used on the patient is determined based on the location of the one or more markers.

In some configurations, the projected markers include a reference marker and at least one sizing marker.

In some configurations, the reference marker is located relative to a reference point or landmark on the face of the patient and the size of the interface is determined based on a location of the at least one sizing marker relative to another reference point or landmark on the face of the patient.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

DETAILED DESCRIPTION

Patient interfaces are used to provide respiratory therapies as treatment for a variety of conditions. Such therapies include non-invasive ventilation (NIV) and positive airway pressure (PAP) therapies, such as continuous positive airway pressure (CPAP), for example. For some respiratory therapies, it is desirable for treatment efficacy and patient comfort that a good fit and seal is achieved between the interface and the patient. As such, it is advantageous to fit a patient with an interface that is a desirable or suitable size for the patient. Certain features, aspects and advantages of the embodiments described herein provide a method and/or apparatus to achieve or facilitate an interface size selection for patients.

In some configurations, the method involves the use of a light source or a plurality of light sources to project sizing one or more markers or indicators onto a patient's face. The markers or indicators are aligned with and used to measure particular facial features or landmarks, thus allowing the selection of an interface size that fits the patient in a desired manner. In some configurations, the method is facilitated by a sizing tool configured to create sizing markers or indicators that correspond to one or more available sizes of an interface or otherwise indicate or allow the determination of an appropriate or desirable interface size (which could involve selection between available sizes of a particular interface or facilitate the determination of a brand or model of interface that provides an appropriate or desirable fit, for example).

In some configurations, the sizing tool is specific to a particular type of interface (e.g., nasal mask or full face mask), brand of interfaces, line or family of interfaces or a single interface. For example, a sizing tool that is particular to a single interface can project sizing markers or indicators onto a patient's face that correspond to the available seal sizes of the interface. The user can determine an appropriate or desirable size of interface or seal based on the marker or indicator located at or most appropriately located relative to particular facial features of the patient. For example, the marker located closest to the relevant facial feature may not indicate the appropriate or desirable size of interface if the marker is on the wrong size of the feature. That is, is may be desirable for the interface seal to contact the patient's face above (or below) the facial feature. Thus, the closest marker located above (or below) the facial feature may indicate the appropriate or desirable size of interface even though another marker is closer to the feature in absolute terms.

In other configurations, the sizing tool is configured or suitable for use with a variety of interface types, brands or lines. For example, the sizing tool can be configured to provide or allow determination of a general measurement or characteristic of the patient's face, such as a distance between two locations (e.g., features or landmarks). The measurement taken by the sizing tool can then be used to select an appropriate or desirable size of interface. For example, the measurement can be compared to data on interface size that relates to the measurement and the comparison of the measurement to the data can facilitate the selection of an appropriate or desirable interface. For example, if the measurement relates to a vertical distance between the sellion and sublabial locations of the patient, that measurement can be compared to the height dimensions of available interfaces or seal sizes to facilitate a selection of an appropriate or desirable interface. Other suitable facial locations, features or landmarks can also be used.

In some configurations, the sizing tool is adjustable and can be adjusted between two or more modes, each of which correspond to a different size, type, family, brand or other classification or identifier of an interface. For example, in some arrangements, the sizing tool has one mode corresponding to one interface type (e.g., full face mask) and another mode corresponding to another interface type (e.g., nasal mask). More than two modes may be provided. For example, there may be three, four, five or any other number of modes. In some configurations the sizing tool comprises a body, a light source supported relative to the body, the light source configured to project a beam of light, one or more light manipulation or control arrangements that manipulate or control the beam of light to project one or more markers onto the face of a patient and wherein a location of the one or more markers corresponds to an interface size. The one or more markers is a portion of the beam of light projected by the light source. In other configurations the sizing tool comprises a plurality of light sources spaced apart from one another along the body, the one or more light sources configured to project a marker on to a user's face, each marker corresponding to an interface size. The markers can be individual light beams from separate light sources or can be portions of a light beam from a single light source. The light manipulation or control arrangements can be beam splitters, prisms, lenses or other devices that can manipulate and/or control light. In some alternative configurations the light manipulation or control arrangements may comprise a light source. In some other configurations the light manipulation or control arrangements may comprise a light source and an associated device that can manipulate, split, bend or otherwise control light. In further alternative configurations the light manipulation or control arrangement can be an optical device that allows light to pass through and affect at least a property of the light, for example speed or direction etc. The sizing tool may comprise an actuator, such as a switch or an on/off button, to activate and deactivate the light source(s).

Figure 1:
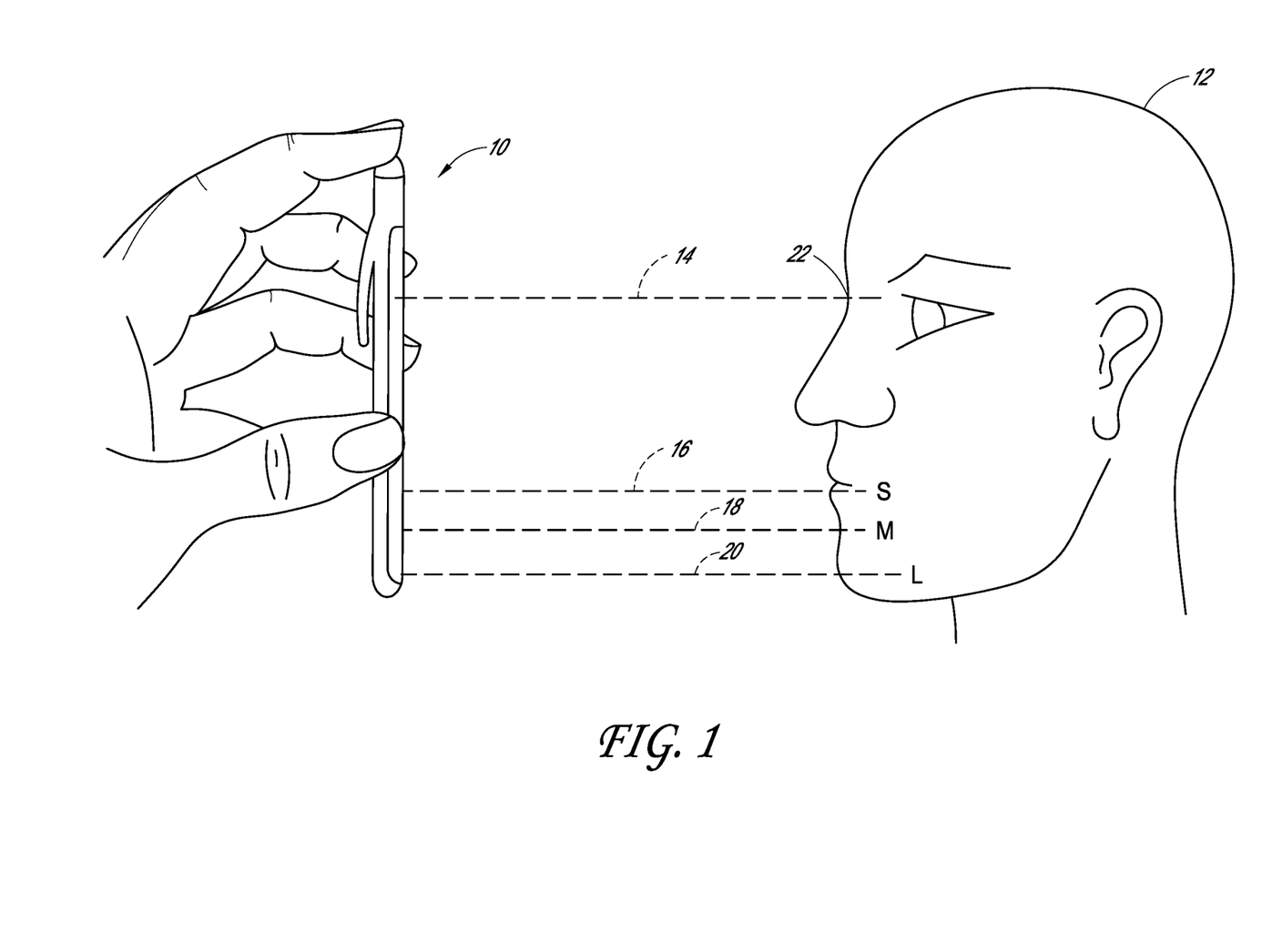
FIG. 1 is a profile view of a sizing tool being used on a patient.

As illustrated in FIG. 1, a sizing tool 10 can be positioned near the face of a patient 12 such that one or more beams of light are projected onto the face of the patient 12. In the illustrated configuration, multiple light beams are projected onto the face of the patient 12. The light beams are markers or indicators that can be utilized by the user of the sizing tool 10 to facilitate selection of an appropriate or desirable size of an interface. In the illustrated arrangement, the sizing tool 10 is similar in size and/or shape to a typical writing pen. Thus, the sizing tool 10 is a handheld device sized, shaped and of a weight that allows the tool 10 to be conveniently held in the hand of a user. The sizing tool 10 can be an elongate member having a length that is significantly greater than the diameter, width or depth. In some configurations, the sizing tool 10 can be about 10-20 cm in length. However, the sizing tool 10 can be provided in other shapes and sizes, including non-portable configurations. For example, the sizing tool 10 may comprise, or be mounted on, a fixed or self-supporting device such as a stand, or bracket or base or the like. The sizing tool 10 may be removably mounted on such a device.

In the illustrated arrangement, a first light beam 14 is a reference light beam, which can be aligned with a particular location, feature or landmark on the face of the patient 12 by the user of the sizing tool 10. One or more additional light beams are projected onto the face of the patient 12 at a location or locations spaced from the first light beam 14. These one or more additional light beams can be utilized to indicate an appropriate or desirable size of an interface.

In the illustrated arrangement, multiple light beams are provided in addition to the first light beam 14. For example, three sizing light beams 16, 18, 20 are provided in addition to the first light beam 14. These light beams 16, 18, 20 are referred to as second, third and fourth light beams, respectively. The second light beam 16, third light beam 18 and fourth light beam 20 can correspond to three different available sizes of an interface, such as small, medium and large, for example. Accordingly, the second light beam 16 can be referred to as the small indicator or marker, or small light beam. Similarly, the third light beam 18 can be referred to as the medium indicator or marker, or medium light beam and the fourth light beam 20 can be referred to as the large indicator or marker, or large light beam. In other configurations, a lesser number (e.g., two) or a greater number (e.g., four or five) of light beams or size indicators or markers can be provided.

In the illustrated positioning of the sizing tool 10, the first light beam 14 is located at an upper location or relatively above or higher than the other light beams 16, 18, 20. In particular, the first light beam 14 is located on the nose of the patient 12, such as at the sellion 22 or the deepest point between the nose and the forehead. However, the first light beam 14 can be located at other locations, such as other facial landmarks or reference points. In some configurations, the location of the first light beam 14 corresponds to a location at which the interface seal contacts the patient 12. In other configurations, the location of the first light beam 14 can be spaced from a location at which the interface seal contacts the patient 12, such as at a landmark that is more easily identified and can be related to a location at which the interface seal contacts the patient 12. Such a landmark can be the sellion 22, for example, in situations in which the interface seal contacts the patient 12 at a location other than the sellion 22. It will be appreciated that an interface seal may not contact all patients at the same location due to the wide variation in facial geometry between patients. Thus, the first light beam 14 can be located at or near a landmark or feature on the face of the patient 12 that is sufficiently close to the location at which the interface seal contacts the patient 12 such that appropriate sizing of the interface can be accomplished.

As illustrated in FIG. 1, the small, medium and large light beams 16, 18, 20 are projected at different locations on the face of the patient 12 when the first or reference light beam 14 is located at the desired location. The small, medium and large light beams 16, 18, 20 are located at different vertical distances from the reference light beam 14. The locations of the small, medium and large light beams 16, 18, 20 may approximate or correspond with locations at which the seals of the small, medium and large interfaces contact the face of the patient 12. The user of the sizing tool 10 can determine which of the small, medium and large light beams 16, 18, 20 is best located relative to a feature or features of the face of the patient 12 to provide a desired fit of the interface. Based on that determination, an appropriate or desired interface size can be selected. For example, in the illustrated arrangement, the user may determine that the small light beam 16 is too close to the mouth of the patient 12 and that the large light beam 20 is too close the chin of the patient 20 such that the small and large interfaces will be undesirably small and undesirably large, respectively. The user may determine that the medium light beam 18 is at the most appropriate location on the face of the patient 12 and determine that the medium interface will provide an appropriate or desirable fit.

Although the reference light beam 14 is illustrated as projecting at a location higher than the locations of the small, medium and large light beams 16, 18, 20, on an upper portion of the face of the patient 12 or on the nose of the patient 12, in other configurations, this orientation could be reversed. For example, the reference light beam 14 could be located lower than the sizing light beams, such as the small, medium and large light beams 16, 18, 20. In some configurations, the reference light beam 14 can be located on a lower portion of the face of the patient 12, such as between the lower lip and chin or at a sublabial point and the sizing light beams (e.g., locations of the small, medium and large light beams 16, 18, 20) can be located on or near the nose of the patient 12 and the appropriate sizing light beam can be selected based on a reference point or landmark on an upper portion of the face of the patient 12.

In one embodiment, certain features, aspects and advantages involve a method and an apparatus involving a sizing or measuring tool 10 in the form of a pen-like structure that is provided with at least one light source and is configured to split, focus and project the light at predetermined spaced locations that correlate to interface sizes so that the projections can be used to measure a patient's face. In use, the measuring tool is held at a distance in front of a patient's face and light markers will be projected onto the face of the patient and used as a measurement scale.

Figure 2:
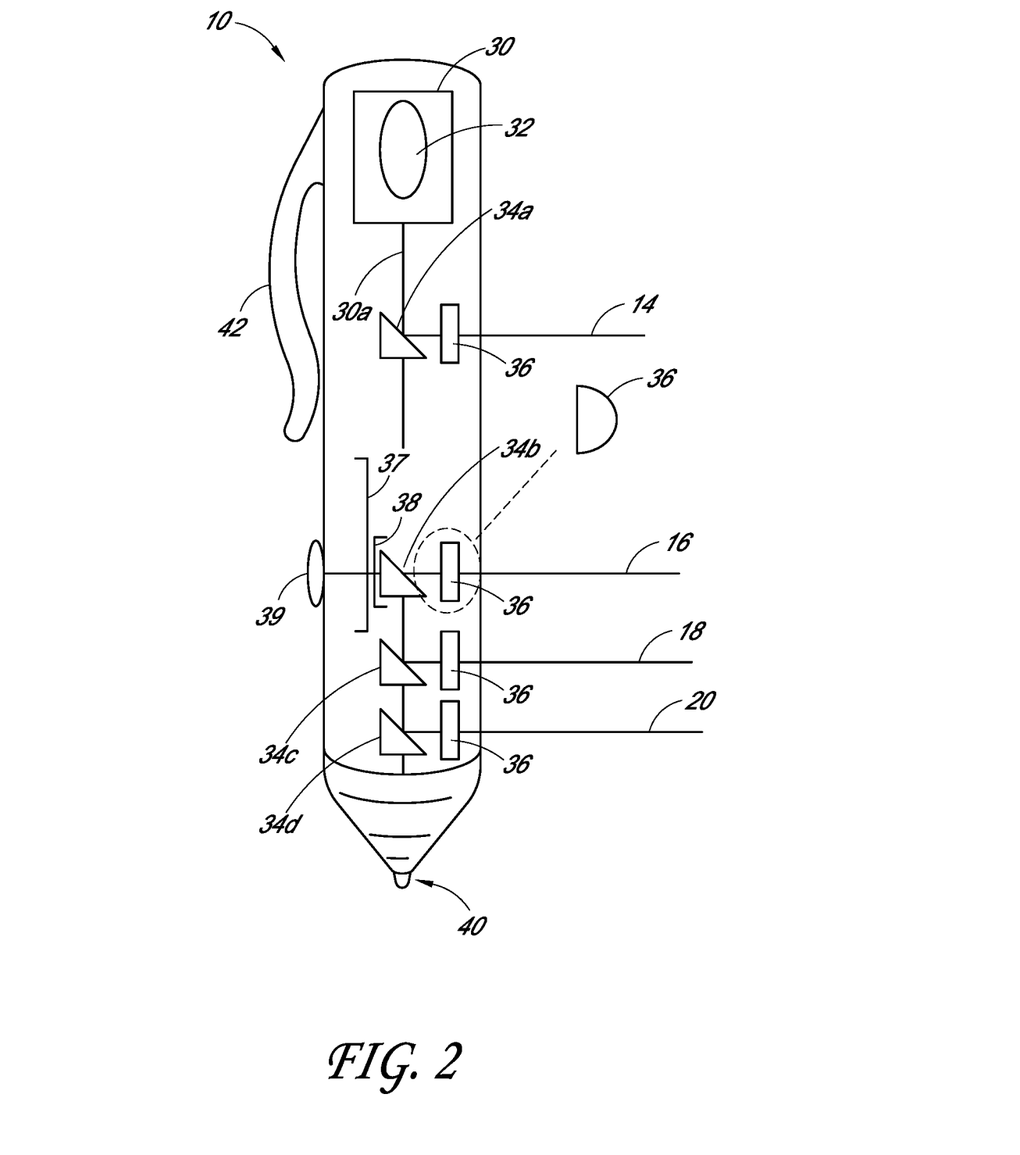
FIG. 2 is a schematic view of a sizing tool having a structure or outward size and/or shape similar to a typical writing pen.

FIG. 2 illustrates a schematic view of one embodiment of the sizing tool 10. The illustrated sizing tool 10 is pen-like in structure in that it is of a similar shape and size to a common writing pen. The pen-like size and shape makes the tool 10 easy to store, carry and handle. The tool 10 includes a light source 30, an on/off button or other control 32, several beam splitters 34 and a lens 36 that refracts and projects the beam emitted from the light source 30.

In some configurations, the light source 30 is a class one laser or LED unit that provides a single beam of light 30a that that is aimed longitudinally along the length of the tool 10. A class one laser provides the advantage of being safe when directed towards a patient's eyes. If an LED light source is used, a focusing system can be provided to create the desired single defined beam of light 30a.

Along the length of the tool 10, there can be a number of beam splitters 34 that cause the beam of light 30a from the light source 30 to be refracted and thus projected from the tool 10 at a predetermined angle. In some configurations, the beam of light is projected perpendicularly to the longitudinal axis of the tool 10 and/or perpendicularly from the direction that the beam of light 30a is projected from the light source 30. In some configurations, there are four beam splitters 34 or one beam splitter 34 for each desired projecting beam or marker. The first beam splitter 34 a can correspond to a reference point used to measure interface size. The beams 16, 18, 20 (FIG. 1) emanating from the three other beam splitters 34 b, 34 c, 34 d, respectively, can correlate to the different interface sizes (e.g., small, medium and large). The three sizing splitters 34 b, 34 c, 34 d are located at points along the tool 10 that correlate to a predetermined geometric feature of the face and/or interfaces. For example, in the case of a full-face interface that encircles the patient's nose and mouth, the reference point can be the bridge of the nose. This means that, when using the tool 10, the first projected marker 14 (FIG. 1) is aligned with the bridge of the patient's nose. This point generally or substantially corresponds to the uppermost contact point that the interface would have with the patient's nose. The sizing splitters 34 b, 34 c, 34 d can be spaced from the reference splitter 34 a such that they match the distance between the bridge of the nose or uppermost contact point of the interface and the lowest sealing point on or under the patient's chin, for each of the interface sizes.

In another embodiment, a manual mechanism can be used to position an individual sizing beam splitter at set positions along the tool that correspond to the different interface sizes. In some such configurations, only two beams of light will be projected onto the patient: a reference marker and a sizing marker. However, multiple sizing markers could be used in such an arrangement. The sizing marker can be moved between the different sizing positions, which can be indicated by the tool, such as by printed indicators, detents or other indicia. The manual adjustment mechanism can be of any suitable arrangement, such as a track 37 and a platform 38 that moves within the track 37 and carries the beam splitter 36, as illustrated in connection with one of the splitters 36 of FIG. 2. The platform 38 can be controlled by any suitable actuation arrangement, such as a twist knob, push-button, sliding switch 39 or other mechanism that adjusts the position of the sizing beam splitter relative to the tool and/or reference marker. In some configurations, an individual beam splitter is provided for each interface size and each of the individual beam splitters can be selectively moved in or out of the path of the light source by the manual mechanism. In such a configuration, there can be two projected markers at any time. In some configurations, a single tool can be used to select sizes for multiple interface families. Having a single tool that can be used to size a patient for a variety of different interface types while not contacting the patient's face, including but not limited to full-face, nasal, pillows and cannula PAP (e.g., CPAP) and NIV interfaces, will make the tool more useful and convenient. A twist knob or other such mechanism can be used to select a particular interface family by moving the beam splitters to positions that correspond to the sizes of the selected interface family.

In some configurations, the light beam is only partially refracted by the beam splitters 34 allowing some of the light to pass through each of the splitters 34 thus reaching the last splitter (e.g., 34d or the splitter 34 further from light source 30) without being completely diminished. Preferably, the light beam reaches the last splitter 34d with enough strength such that the last light beam 20 (FIG. 1) produces a visible marker on the face of the patient 12. The beam splitters 34 can be of a triangular geometry or any other geometry that is capable of refracting the light beam by a predetermined or other desirable angle.

In front of each beam splitter 34 can be a lens 36 that manipulates the refracted light beam. For example, the lens 36 can be configured to further refract the beam of light so that a line of light is projected onto the patient's face rather than a single point of light. In order to achieve this refraction the lenses 36 can have a semi-circular or half-round cross-sectional profile. The lenses 36 can be made from acrylic glass (e.g., poly methyl methacrylate) or other materials with similar optical properties. In some embodiments, a single lens extends the entire length of the sizing tool and interacts with some or all of the refracted light beams 14, 16, 18, 20.

In some embodiments, the tool 10 incorporates a pen or laser pointer device 40 at the end opposing the light source 30. This arrangement provides the tool 10 with a secondary purpose and makes it more useful and hence more likely to be used. Other common characteristics of pens, such as a pocket clip 42 or lanyard attachment can be included to increase ease of use and convenience.

Figure 3A:
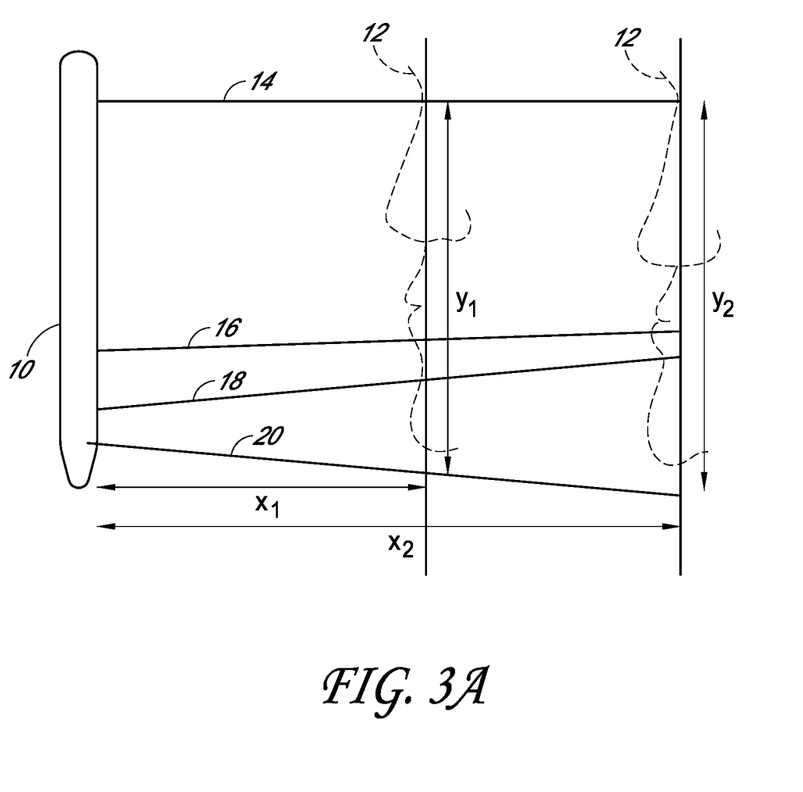
FIG. 3A a diagram that demonstrates the effect of non-parallel light beams.

Alignment of the beam splitters 36 can have an impact on the usability and accuracy of the tool 10. The beam splitters 36 can be angled to direct the refracted light beam at a predetermined angle relative to the direction of light beam 30*a* from the light source 30. Preferably, each of the beam splitters 36 is configured to refract the light such that each of the split beams 14, 16, 18, 20 is parallel to the others. This arrangement reduces the likelihood of distortion of the distance between projected markers as the tool 10 is held at different distances from the patient 12 being measured, as shown in FIG. 3A. FIG. 3A illustrates an exaggerated view of the distortion of the distances Y1 and Y2 between projected reference and sizing markers 14 and 20, respectively, that result from non-parallel beams when the tool 10 is held at different distances X1 and X2 from the patient 12. Although not specifically designated, FIG. 3A illustrates distortion of sizing markers 16 and 18 as a result of being non-parallel with reference marker 14.

Figure 3B:
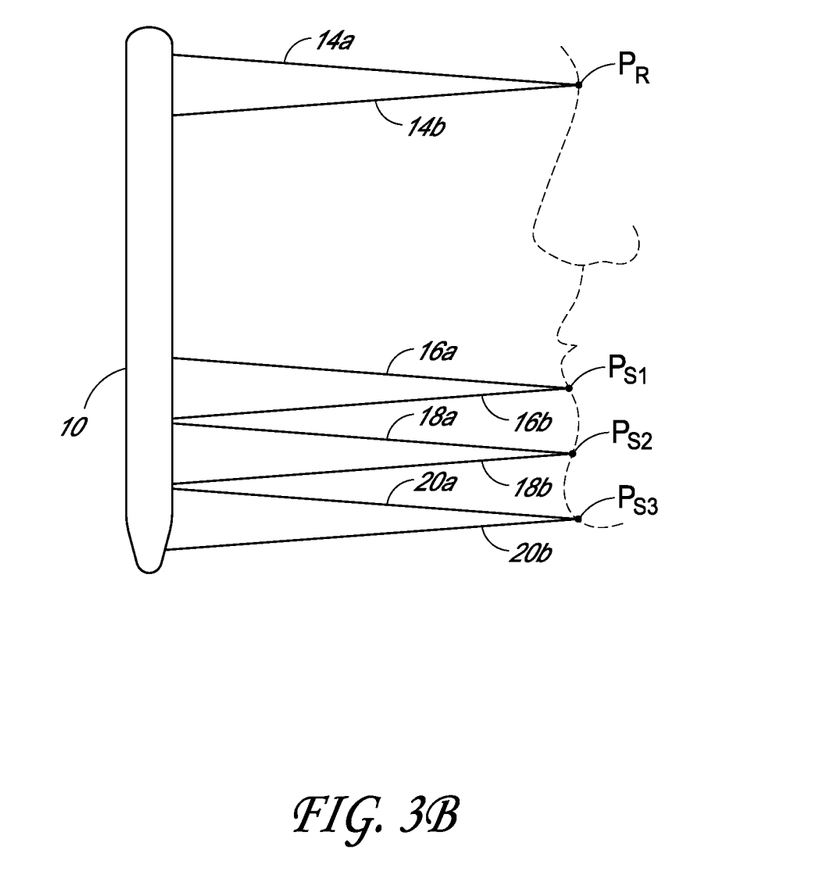
FIG. 3B is a diagram of an embodiment having two light beams for the reference marker and each sizing marker.

In some configurations, the tool 10 can include two or more light sources. In configurations using two light sources, as illustrated in FIG. 3B, the light sources can be refracted to create two beams for each of the sizing markers (16*a*, 16*b*, 18*a*, 18*b*, 20*a*, 20*b*) and the reference marker (14*a*, 14*h*). When the tool is held at the predetermined distance and angle to the patient's face, the refracted beams will intersect with each other to create a single focused marker point ($P_R$, $P_{S1}$, $P_{S2}$, $P_{S3}$) on the patient's face (i.e., each sizing marker and the reference marker will be generated by two light beams). Such an arrangement can reduce or minimize any measurement distortion generated as a result of the tool 10 being held at an incorrect angle or distance from the patient's face by allowing the user to determine when the tool 10 is held at the correct distance. That is, the user can adjust the distance of the tool 10 relative to the patient's face until one or more of the reference marker and sizing marker(s) project a point on the patient's face (or line in the case of a line marker, as described above).

In at least one configuration, the light beam from the light source 30 can be further split or manipulated and used to project symbols onto the face of the patient 12, which symbols may indicate which interface size each of the projected markers correlates to (e.g., an 'S', 'M', or 'L' can be used to indicate 'small', 'medium' and 'large' respectively). The symbols can be configured to come into focus when the tool is held an appropriate distance from the patient's face, similar to the arrangement described above, to provide an indication to the user of when the tool 10 is at a proper distance. In some configurations, individual light sources can be used to project the symbols or one or more (e.g., each) of the reference or marker light beams.

Figure 4:
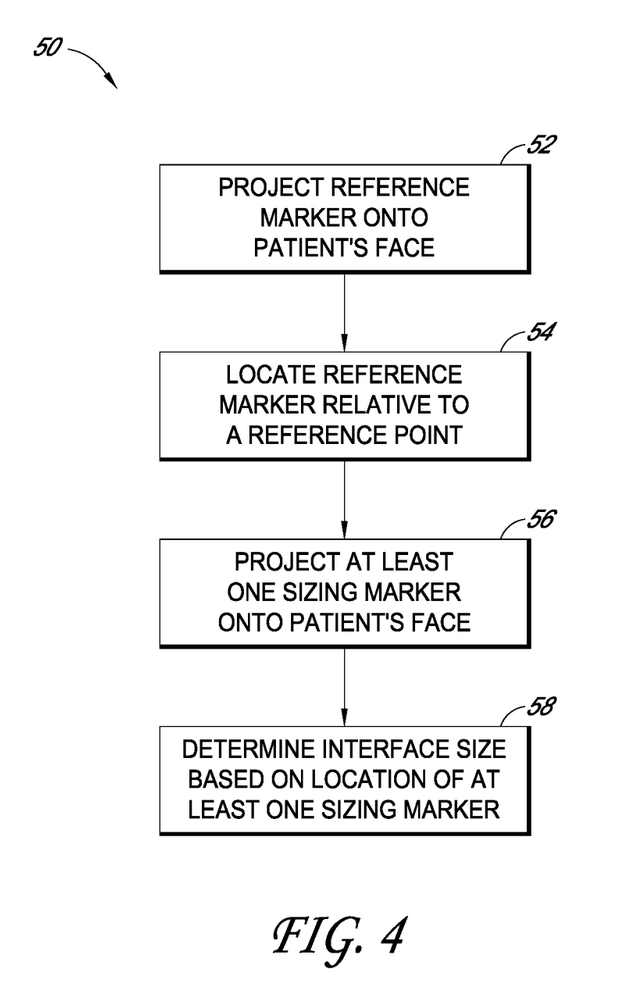
FIG. 4 is a block diagram of an exemplary process for determining an appropriate or desirable interface size for a patient.

FIG. 4 illustrates a block diagram of a method or process 50 for determining a size of an interface for a particular patient. The process 50 can utilize a sizing tool, such as any of the sizing tools 10 disclosed herein, or can utilize other types of sizing tools or other devices for projecting beams of light onto the face of a patient. As described herein, determining an appropriate or desirable size of interface can include selecting a particular interface or seal size between available sizes of a particular interface. The determining of an appropriate or desirable size can broader in scope, such as determining an appropriate brand or model of interface for the particular patient.

At block 52, a reference marker is projected onto the face of the patient. The reference marker preferably is a beam of light, which can be a point, a line or another suitable shape as projected on the patient. The reference marker preferably is projected by a user of a sizing tool by powering on the tool, if necessary, and positioning the tool at a suitable location and orientation relative to the patient's face such that the reference marker is projected onto the patient's face.

A block 54, the reference marker is located relative to a reference point or other location on the patient's face. The reference marker can be located at the reference point or location or can be located at a distance from a reference point (e.g., 5 mm below the sellion). The reference point or location can be any suitable feature or landmark on the patient's face and, in at least some configurations, is located at, near, relative to or otherwise corresponds to a location on the patient's face that is contacted by the interface seal. The reference point can be located at or near an uppermost point of contact between the interface seal and the patient or a lowermost point of contact between the interface seal and the patient. In other arrangements, sizing may be determined by a horizontal measurement, in which case the reference marker can be located at a suitable lateral location on the patient's face (e.g., outward of one side of the mouth).

At block 56, a least one sizing marker is projected onto the patient's face. In some configurations, multiple sizing markers are projected onto the patient's face. The multiple sizing markers can correspond to available sizes of an interface, for example.

At block 58, a size of interface is determined based on a location of the at least one sizing marker on the patient's face. Preferably, the user of the sizing tool or other projecting device makes the determination based on the location of the sizing marker(s). The determination can involve the location of the sizing marker(s) relative to a landmark or other feature of the patient's face. In some configurations, the sizing landmark or feature is located at, near, relative to or otherwise corresponds to a location on the patient's face that is contacted by the interface seal. The sizing landmark or feature can be located at or near a lowermost point of contact between the interface seal and the patient or an uppermost point of contact between the interface seal and the patient. In other arrangements, sizing may be determined by a horizontal measurement, in which case the reference marker can be located at a suitable lateral location on the patient's face (e.g., outward of one side of the mouth). In configurations with multiple sizing markers, the determination can involve selection of the sizing marker most appropriately located relative to the sizing landmark or feature, which can be the closest marker in absolute terms or can be the closest marker that is appropriately positioned relative to the sizing landmark or feature. For example, the appropriate sizing marker can be the marker closest to the sizing landmark or feature that is located on a particular side (e.g., above, below, inward or outward) of the sizing landmark or feature.

The activities associated with blocks 52, 54, 56 and 58 are not necessarily performed in the order illustrated and described. For example, in some configurations, the projection of the reference marker and sizing marker(s) can occur simultaneously. In addition, other activities can be performed as well. For example, the sizing tool can be moved to focus a reference marker or other location indicator on the patient's face to verify proper location of the sizing tool, as described above. In some configurations, the process includes moving the location of a sizing marker relative to the reference marker. In such configurations, the determination of an appropriate or desirable interface size can involve determining the position of the sizing marker relative to the reference marker once the sizing marker is located at an appropriate or desirable distance from the reference marker. For example, the user can read the location of the sizing marker based on location indicia provided on the sizing tool (e.g., a size scale or detent location).

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. An interface sizing tool, comprising:
    a body;
    at least one light source supported relative to the body, the at least one light source configured to project at least one primary beam of light;
    one or more light manipulation arrangements configured to manipulate the at least one primary beam of light to project a reference marker and one or more sizing markers onto the face of a patient;
    wherein each of the one or more sizing markers comprises two light beams that are configured to intersect one another to create a single focused sizing marker point on the face of the patient when the tool is held at a predetermined distance and angle to the face of the patient,
    wherein a location of the single focused sizing marker point of the one or more sizing markers corresponds to an interface size.

2. The interface sizing tool of claim 1, wherein the reference marker comprises two light beams that are configured to intersect one another to create a single focused reference marker point on the face of the patient when the tool is held at the predetermined distance and angle to the face of the patient.

3. The interface sizing tool of claim 1, wherein multiple light manipulation arrangements are provided.

4. The interface sizing tool of claim 1, wherein each of the one or more light manipulation arrangements comprises a beam splitter.

5. The interface sizing tool of claim 1, wherein the one or more light manipulation arrangements comprises multiple beam splitters spaced apart from one another on the body, wherein the multiple beam splitters are configured to generate the reference marker and the one or more sizing markers.

6. The interface sizing tool of claim 5, wherein the multiple beam splitters are shaped and spaced such that the reference marker and each of the one or more sizing markers are spaced a predetermined distance from one another.

7. The interface sizing tool of claim 6, wherein the spacing between the reference marker and each of the one or more sizing markers corresponds to the size of the interface.

8. The interface sizing tool of claim 5, wherein the one or more light manipulation arrangements further comprise at least one lens positioned in front of the beam splitters and configured to focus an associated one of the two light beams of the sizing maker and a light beam of the reference marker.

9. The interface sizing tool of claim 1, wherein the one or more sizing markers comprises multiple sizing markers, each of which is visible on the face of the patient at the same time.

10. The interface sizing tool of claim 1, wherein the one or more sizing markers comprises a single sizing marker that is movable along a length of the body.

11. The interface sizing tool of claim 10, wherein the single sizing marker is movable to two or more positions relative to the body corresponding to two or more interface sizes.

12. The interface sizing tool of claim 11, wherein a mechanism for moving the single sizing marker comprises a push button, a twist knob or a sliding switch.

13. The interface sizing tool of claim 1, wherein the body comprises a clip that permits the tool to be attached to an object by the clip.

14. The interface sizing tool of claim 1, further comprising a laser pointer or writing tip.

15. The interface sizing tool of claim 1, wherein the tool is configured to indicate an interface size of a patient while not contacting a face of the patient.

16. A method of sizing a patient for a respiratory interface, comprising:
    using an interface sizing tool to project a reference marker comprising at least one beam of light onto the face of a patient;
    using the interface sizing tool to project one or more sizing markers onto the face of the patient, wherein each of the one or more sizing markers comprises two light beams that intersect one another to create a single focused sizing marker point; and
    determining a size of the respiratory interface to be used on the patient based on the location of the reference marker and the one or more sizing markers.

17. The method of claim 16, wherein the determining the size of the interface to be used on the patient is done without contacting the patient with the interface sizing tool.

* * * * *

UNITED STATES PATENT AND TRADEMARK OFFICE
CERTIFICATE OF CORRECTION

PATENT NO. : 10,569,040 B2  
APPLICATION NO. : 16/111029  
DATED : February 25, 2020  
INVENTOR(S) : Andrew Grant Niccol It is certified that error appears in the above-identified patent and that said Letters Patent is hereby corrected as shown below:

In the Specification

In Column 4, Line 6, delete "3A" and insert --3A is--.

In Column 9, Line 34, delete "14h)." and insert --14b).--.

In the Claims

In Column 12, Line 26, Claim 8, delete "maker" and insert --marker--.

Signed and Sealed this  
Nineteenth Day of May, 2020

Andrei Iancu  
*Director of the United States Patent and Trademark Office*